US006556299B1

United States Patent
Rushbrooke et al.

(10) Patent No.: US 6,556,299 B1
(45) Date of Patent: Apr. 29, 2003

(54) IMAGING SYSTEM FOR FLUORESCENCE ASSAYS

(75) Inventors: John Gordon Rushbrooke, Cambridge (GB); Claire Elizabeth Hooper, Cambridge (GB); William Wray Neale, Cambridge (GB)

(73) Assignee: Packard Instrument Company, Inc., Meriden, CT (US)

( * ) Notice: Subject to any disclaimer, the term of this patent is extended or adjusted under 35 U.S.C. 154(b) by 0 days.

(21) Appl. No.: 09/214,919

(22) PCT Filed: Jul. 4, 1997

(86) PCT No.: PCT/GB97/01826

§ 371 (c)(1),
(2), (4) Date: Feb. 15, 2000

(87) PCT Pub. No.: WO98/01744

PCT Pub. Date: Jan. 15, 1998

(30) Foreign Application Priority Data

Jul. 10, 1996 (GB) .............................................. 9614528
Oct. 1, 1996 (GB) .............................................. 9620437
Dec. 3, 1996 (GB) .............................................. 9625132

(51) Int. Cl.[7] .............................................. G01N 21/64
(52) U.S. Cl. .................................... 356/417; 250/458.1
(58) Field of Search ....................... 356/417; 250/458.1, 250/459.1, 461.1, 461.2

(56) References Cited

U.S. PATENT DOCUMENTS 4,922,092 A * 5/1990 Rushbrooke et al. . 250/214 VT
5,347,122 A * 9/1994 Ansorge et al. ........ 250/227.11

* cited by examiner

Primary Examiner—F. L. Evans
(74) Attorney, Agent, or Firm—Barnes & Thornburg

(57) ABSTRACT

An imaging system for fluorescence assays includes a fiber optic coupling plate (20, 24, 26) for transmitting radiation emitted by a sample (18) towards a camera. This is combined with an interference filter (22) so as to enable highly sensitive transmission of radiation to the camera, according to wavelength. The interference filter may be combined with a fiber optic coupling plate in which sample sites or wells of an array are viewed by separate fiber optic bundles, each bundle transmitting emitted light from a one sample or well to a discrete region of the field of view of the camera.

16 Claims, 10 Drawing Sheets

TAPER I/P FACE

OUTPUT FACE TO
INTERFERENCE FILTER

IMAGING SYSTEM FOR FLUORESCENCE ASSAYS

FIELD OF INVENTION

This invention concerns methods and apparatus for imaging, particularly the imaging of fluorescing samples of the type in which the sample is first illuminated with an excitation radiation such as ultra-violet light, and is subsequently interrogated for any resulting emission light due to fluorescence within the sample.

BACKGROUND TO THE INVENTION

U.S. Pat. No. 4,922,092 describes a fibre optic device used to couple the light emitted from an array of well sites in a plate to an imaging device.

Our concurrent International Patent Application No. PCT/GB97/01825, filed Jul. 4, 1997, describes alternative arranges and systems incorporating fibre optic devices by which a large number of well sites can be inspected for fluorescence arising therefrom.

It is an object of the present invention to provide an improved optical fibre transfer device and an improved method of coupling the output of such a device to a camera input.

In FIGS. 10 and 11 of our concurrent Application, the output end of the fibre optic plate is shown coupled to a camera input window via a filter. The purpose of the filter is to restrict wavelengths entering the camera to those of expected, or wanted, emissions so as to ideally remove from the camera input any radiation at unwanted wavelengths such as stray excitation radiation transmitted via the fibre optic plate, or the like.

In an example involving 96 fibre optic bundles, the 96 outputs of the bundles may be arranged in any convenient configuration or aspect ratio depending on the output of the camera to which the image is to be applied. Where the latter is generally circular, the 96 rods may be arranged in a generally circular or hexagonal array so as to substantially fill the entrance window of the camera, and if the latter is 40 mm diameter and the rods fill an area of $32 \times 42$ mm$^2{}_1$, there should be adequate spacing between rod centres (approximately 2.5 mm) to ensure minimal cross-talk between bundles. Where an emission filter is inserted between the plate and the camera input, this should be as thin as possible, and may need to be less than 0.5 mm to ensure acceptable levels of cross-talk.

Since the excitation wavelengths may be very close to the wavelengths of emitted radiation from the samples or where two or more emitted radiations can arise and selection as between one wavelength and another is desired, the difference between the wavelengths of the different emitted radiations may be very small. In these circumstances ordinary filters may not be sufficiently selective.

THE INVENTION

According to the present invention in an imaging system for fluorescence assays, a fibre optic coupling plate for transmitting radiation emitted by a sample towards a camera, is combined with an interference filter so as to enable highly selective transmission of radiation to the camera, according to wavelength.

The present invention also envisages the combination of an interference filter with a modified fibre optic coupling plate such as described herein, in which the sample sites or wells of an array thereof are viewed by separate fibre optic bundles, and each bundle transmits emitted light from a one sample or well to a discrete region of the field of view of the camera.

Typically the interference filter is located between the output end of the fibre optic coupling plate and the camera input window.

Where a system is intended to operate at a single wavelength, the interference filter may form part or comprise the input window of the camera.

Where, as is more likely, the system is to be capable of handling different assay chemistries and selection of different wavelengths, provision may be made for interchanging the filter so as to render the camera more or less sensitive to different wavelengths.

In one arrangement, two or more interference filters may be located in apertures in a slidable or rotatable support plate located between the output side of the fibre optic coupling plate and the input window of the camera, and the filter support plate filters is movable so as present one or another of the filters to the camera as appropriate.

The movement may be effected manually, or drive means may be provided, to effect the movement to position different filters in place.

Where the inspection system is computer controlled, the control system may be programmed to move the filter support plate according to the assay chemistry and/or wavelengths involved, or may be programmed so as to present a sequence of different filters during the course of inspection of each set of well sites, and the camera output is switched or flagged accordingly, so as to allow the different filters to be linked to the different camera output signals.

Use of an interference filter instead of an absorption filter allows improved discrimination of emission wavelengths and the improved blocking of unwanted wavelengths, whether residual excitation reduction or other emissions arising from the excitation.

The use of an interference filter may however introduce two problems.

Such a filter is quite thick (eg 5–10 mm), which can lead to cross talk between well emissions due to loss of spatial resolution. Furthermore, the central wavelength of the bandpass range shifts with angle of incidence eg at 15° from the normal to the filter, the shift is typically 4 nm. This may be acceptable in many instances but at 30°, the shift is typically 16 nm, which is almost certainly unacceptable.

One solution is to compromise light gather efficiency by using fibre optic bundles having smaller numerical aperture of say 0.6 instead of 1. However this will not limit the angle of extreme rays ($\sin^{-1} 0.6 = 37$).

Since it is a primary requirement of systems such as described herein, (and. in our concurrent Application) that fibre optic bundles are used having a high numerical input aperture (ie angular acceptance), the numerical aperture of the output end of the fibre optic bundle will also be high. This results in a large cone of rays emanating from the end of each fibre towards the filter. This is generally incompatible with the input requirements of an interference filter which operate best when input rays have only a small angular spread.

According therefore to a further feature of the present invention, optical means is incorporated which effectively reduces the numerical aperture of the output of the coupling plate as seen by the interference filter.

In a preferred arrangement, optical means is provided which cause the light emitted from the coupling plate to be converted into a parallel beam.

In one arrangement magnifying optical means is provided between the output face of the coupling plate and the interference filter so as to present an enlarged image of the coupling plate output face, to the interference filter.

Typically a separate lens is required for each fibre optic bundle. In such an arrangement a mini-lens or a gradient index (GRIN) lens may be placed at the end of each bundle of optical fibres.

Disadvantages of a lens approach include wavelength dependence of the optics, vignetting, limited acceptance numerical aperture, difficulty of restricting angular range of skew rays or rays coming from the edges of the optical fibres and the need for careful alignment of lenses with the fibres.

Alternatively and more preferably, the fibres making up the bundles may increase in cross-section as between the input and output ends of the plate, so as to present an enlarged image of the well emissions to the interference filter.

According to a preferred feature of the invention, therefore a preferred solution involves the use of a fibre optic coupling plate in which the fibres taper in cross-section from the output end to the input end so that the area of each fibre and therefore each fibre optic bundle in the output face of the plate is greater than that of the particular fibre or fibre optic bundle in the input face of the plate.

Typically the size ratio between the input and output ends of the plate is 15.45.

Typically the diameter of the camera input is 45 mm and a well plate has 96 wells, which therefore require there to be 96 fibre optic bundles. Conveniently the 96 fibre optic bundles are arranged in a hexagonal array in the output face of the coupling plate. The input diameter end of the bundles is typically 0.6 mm, and these are typically arranged with a 1 mm spacing. The angular spread of rays leaving a bundle and entering an interference filter thus will be reduced to one third of that of rays entering the end of the bundle, and will typically be of the order of 120, so reducing the wavelength shift to only 3 nanometres. With a 7 mm thick interference filter there should be negligible cross-over of rays between adjacent fibre optic bundles, since the output ends of the bundles will have a diameter of 1.8 mm.

In either event (using lenses or tapering fibres), the larger image presented to the interference filter results in a smaller angular spread of light rays so that the interference filter is able more readily to function and discriminate between one wavelength and another.

As mentioned previously, preferably a small air gap exists on opposite sides of the interference filter to enable it to be removed and replaced with a different interference filter as required, for example by means of a filter wheel. By keeping the air gaps small typically in the range 0.1 to 0.2 mm, negligible spreading of light from the ends of the fibre optic bundles will occur.

The preferred arrangement avoids most of the problems associated with mini lenses or GRIN lenses. There is negligible wavelength dependence, little vignetting, high input numerical apertures are readily obtained, and such problems as remain (in general relatively small by comparison) extreme stray and skew rays and geometrical alignment.

According to a further preferred feature of the invention, in addition to the use of a magnifying fibre optic plate as aforesaid, a further optical device may be used to advantage between the output end of the magnifying coupling plate and the camera input so as to substantially exclude extreme stray and skew rays from the input to the camera.

In a preferred arrangement the image formed on the output of the magnifying coupling plate may be focused onto the camera input by means of an optical lens. Since the angular spread of non-extreme rays of light from any point on the coupling plate output face will be 12° or less, (measured in air), most of the light leaving the output face of the plate can be collected by a lens having an acceptance aperture of f1.2. Such a lens is readily constructed typically as a multi-element lens and the advantage is that rays greater than 12° such as extreme, stray and skew rays will not be collected by the lens. The presence of the lens therefore will tend to eliminate cross-talk between light emanating from the output of adjacent fibre optic bundles and light with large wavelength shifts. Furthermore it will also facilitate the manipulation of interference filters since a larger air gap between coupling plate and filter can be permitted.

Where the diameter of the faceplate and camera inputs have been matched, the lens preferably has unity magnification.

Where any mismatch exists between the output face of the coupling plate and the camera input, this can be accommodated by using a lens of appropriate magnification.

Alternatively the optical lens may be replaced by a second fibre optic coupling plate in which separate fibre optic bundles are held in a spaced array to define an input face in which the size, spacing and arrangement of the fibre optic bundle ends corresponds to those forming the output face of the coupling plate between the interference filter and the reaction sites, and wherein the opposite ends of the fibre optic bundles are arranged so as better to conform to the camera input size and/or aspect ratio. Where the latter has a rectangular field of view, the output ends of the fibre optic bundles may be arranged in a rectangular matrix of appropriate dimensions so as to be accommodated within the input window of the camera.

The optical fibres making up the bundles in the second coupling plate may vary in cross-section from input to output so as to present either an enlarged or a reduced size image or may be of constant cross-section so that there is no magnification or demagnification between input and output of the second coupling plate.

Where any lens or other optical element is employed, preferably this is corrected chromatically for the wavelengths expected to be handled by it.

Where two or more wavelengths are to be investigated requiring two or more filters it may be simpler and cheaper to construct matching pairs of interference filter and lens, (or interference filter and second coupling plate), each element of each pair being chromatically corrected for the wavelength(s) it is intended to be used with and each filter and lens (or coupling plate), is mounted in a cylindrical passage extending between two faces of a support member adapted to be moved, (such as rotated) so as to present first one and then another of the pairs of elements in the path between the first coupling plate output and the camera input.

Where air gaps are required between fibre optic bundle ends and interference filters and the like, it has been found that air gaps of up to 0.5 mm can be accommodated, although for many reasons smaller air gaps are preferred.

According to a further aspect of the invention, the primary coupling plate may be constructed quite differently so as to avoid the need for the sequential presentation of different interference filters between the output and the camera. In this arrangement non-tapering optical fibres (or fibres in which the taper is reversed so that each fibre output end is smaller than its input end) may be used. The output end of each bundle of fibres is well spaced from adjoining fibre optic bundle ends and an interference filter having an appropriate central (or peak) wavelength is positioned between the output face of the coupling plate and the camera so that emissions of different wavelength from a fibre optic bundle appear at different diameters on the output face of the filter relative to the position of the centre or peak wavelength emissions from the relevant optical fibre bundle.

Provided the pixel resolution of the camera is high enough, the different diameter rings of light corresponding to the different wavelengths emanating from each fibre optic end can be identified and measured using standard image processing techniques.

It is an advantage of such a method that where different wavelengths are expected from an assay, and both or all need to be checked before the analysis can be completed, all of the wavelengths emissions can be checked during a single inspection period, instead of during a succession of such periods.

Where the assay period is for example 10 minutes or longer, the saving in time if (say) three different wavelengths are to be investigated, is considerable.

According to a further aspect of the invention the transmission of skew rays arising in the apparatus is reduced by substituting an angle collimating plate for the lens or second coupling plate.

The collimating plate may be constructed from a plurality of optical fibres arranged in a bundle, each of which has a low numerical aperture (NA).

A typical NA for each optical fibre would be 0.2.

The optical fibres making up the bundle are preferably fused into a unitary plate.

The plate is preferably located just in advance of the fibre optic input plate of the camera.

Alternatively the plate may be integrated into or comprise the fibre optic camera input plate.

According to still another aspect of the invention, multiple wavelength emission analysis of fluorescent arrays producing up to N different wavelength emissions is achieved by providing a fibre optic device having input and output faces between the fluorescing samples and the interference filter which divides the emitted light into N different paths, each of which presents its fraction of the emitted light over one of N different discrete regions in the output face of the device, and N different interference filters are located in the light path between the output face and the camera input faceplate, each registering with one of the said N discrete regions in the output face of the device, and each of the N filters being selective of a unique one of the N different wavelengths which can arise in the emitted light.

Each of the N different paths in the device nay be made up of one or a plurality of optical fibres.

The cross-section of each fibre path or number of fibres in each path, may be the same for each of the said N paths, or may be different. Where light of one wavelength is emitted at a low level, larger areas of fibres (or number of fibres) may be provided for supplying light to the relevant discrete regions and associated filter, for that wavelength, to ensure there is a sufficient quantity of light of that wavelength at the camera input, to register.

Where the quantity of light of different wavelengths is to be compared one with another, so as for example to allow a ratio (or series of ratios) to be obtained, each of the N light paths should have substantially the same light transmission characteristics (disregarding the filter), but where this is not the case, or where the light capturing and transmitting capabilities of one or more paths is enhanced relative to the others, a scaling factor may be determined and stored for adjusting the camera output signals relating to the received light from each such enhanced path.

The different paths and filters may have differing light transmitting characteristics which may be inherent or due to manufacturing tolerances, or both. To this end the camera is preferably calibrated using standard light emitting devices producing known levels of light emission at selected wavelengths, and a look up table of scaling factors is created for adjusting the camera output signals during subsequent analysis scans, so as to normalise the output signals corresponding to the different paths and thereby allow a more accurate assessment of the relative values of the different wavelengths to be obtained.

N will usually only be 2 or 3, although the invention is not limited to such small numbers of different paths.

The invention will now be described by way of example with reference to the accompanying drawings, in which.

DETAILED DESCRIPTION OF DRAWINGS

Figure 1:
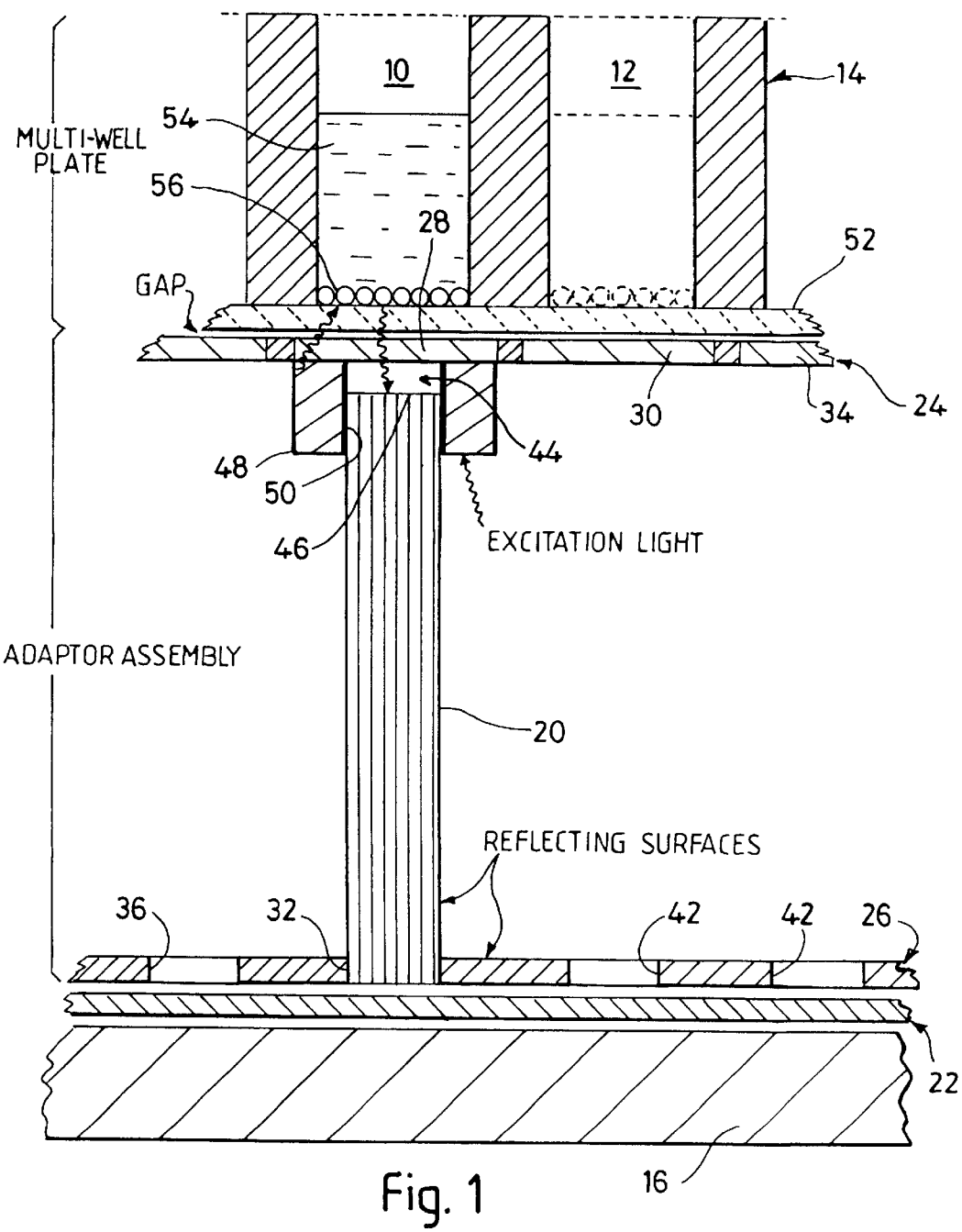
FIG. 1 is a cross-section to an enlarged scale illustrating an embodiment of an imaging system in accordance with our concurrent Application.

In FIG. 1 two wells 10 and 12 forming part of a multiwell plate generally designated 14 are shown in the upper part of the drawing and a camera input window 16 is shown in the lower part of the drawing. Light emitted by a sample such as 18 in well 10 is conveyed via a fibre optic bundle 20 to the camera via a filter 22 which serves to remove unwanted wavelengths such as excitation wavelengths and spurious emissions should they occur.

The fibre optic bundles 20 are carried between two opaque plastic plates 24 and 26 which are separated and held together by a boundary wall (not shown) to form a hollow box through which the fibre optic bundles 20 extend.

The upper plate 24 is apertured as at 28 and 30, 32 and 34 and the lower plate 26 is likewise formed with openings through which the fibre optic bundles such as 20 extend. These openings are shown at 36, 38 (in the case of fibre optic bundle 20), 40 and 42.

For clarity only fibre optic bundle 20 is shown in FIG. 1, but it will be appreciated that similar bundles extend below each of the apertures 30, 32 and 34 to extend across to the apertures 40, 36 and 42 respectively in the lower plate.

In a typical arrangement, there may be as many as 96 wells in the well plate 40 and likewise 96 fibre optic bundles such as 20 which extend in alignment with each of the wells.

As shown, each of the windows such as 28, is a solid clear polystyrene material through which light can pass.

A transparent plug 44 occupies the space between the underside of the window 28 and the input face 46 of the respective fibre optic bundle 20. Typically clear polystyrene is used for the material of the plug. Alternatively the plug may be formed from a filter material so as to further assist in removing unwanted wavelength from the light passing through the fibre optic bundle 20.

An annular sleeve 48 also of polystyrene material surrounds the upper end of the fibre optic bundle 20 and the clear polystyrene plug 44. The inside cylindrical surface 50 of the sleeve 48 is formed with an opaque, possibly reflective, material so as to restrict the loss of light from any fluorescence which occurs within the sample and also restrict the entry of excitation radiation directly into the upper end 46 of the fibre optic bundle 20.

The outside surface of the fibre optic bundle or the external surface of each of the fibres making up the bundle is coated with a reflective material such as titanium dioxide. In a similar manner the inside surfaces of the two plates 24 and 26, (except where apertures or windows are formed therein) are also coated with a similar reflecting material.

The coating material is selected so as to be opaque to excitation wavelengths so as to prevent the ingress of excitation radiation into the fibre optic bundles.

In order to stimulate fluorescence, excitation radiation is directed into the hollow space between the two plates 24 and 26 and by appropriate selection of the material forming the annular sleeves, some of this radiation will pass through the sleeve material, through the clear polystyrene windows such as 28 and 30, through the material forming the base of the well plate designated by reference numeral 52, and into the assay contained within the well.

In known manner the assay includes materials which if subjected to excitation radiation will fluoresce at known wavelengths and it is the fluorescent emission radiation which is transmitted via the base 52 and window such as 28 into the fibre optic bundle 20 associated with the well concerned.

In the well 10, there is a liquid 54 and solid material 56, which may comprise phosphor coated particles having part of the assay on their surface. In accordance with known techniques the other labelled phase of the assay exits in or is introduced into the liquid, and the binding of the two parts of the assay is indicated by the degree of fluorescence from the sample.

The optical fibres making up the bundle 20 are grouped together and are touching so as to form a rod and there are no spaces between the fibres through which excitation radiation can enter and along which such radiation can pass into the well 10. Instead all excitation radiation entering the well must pass through the annular sleeve 48.

The latter may be formed from polystyrene which may be translucent, as opposed to transparent, so as to diffuse any radiation passing therethrough to produce more even illumination of the well.

The fibre optic bundles making up the transfer rods can be grouped differently at the output end of the plate from the arrangement at the input face of the plate, in which the number and spacing and size is dictated by the arrangement of the wells in the sample plate. This enables any desired arrangement or pattern of fibre optic bundle ends to be presented to the filter.

Figure 2:
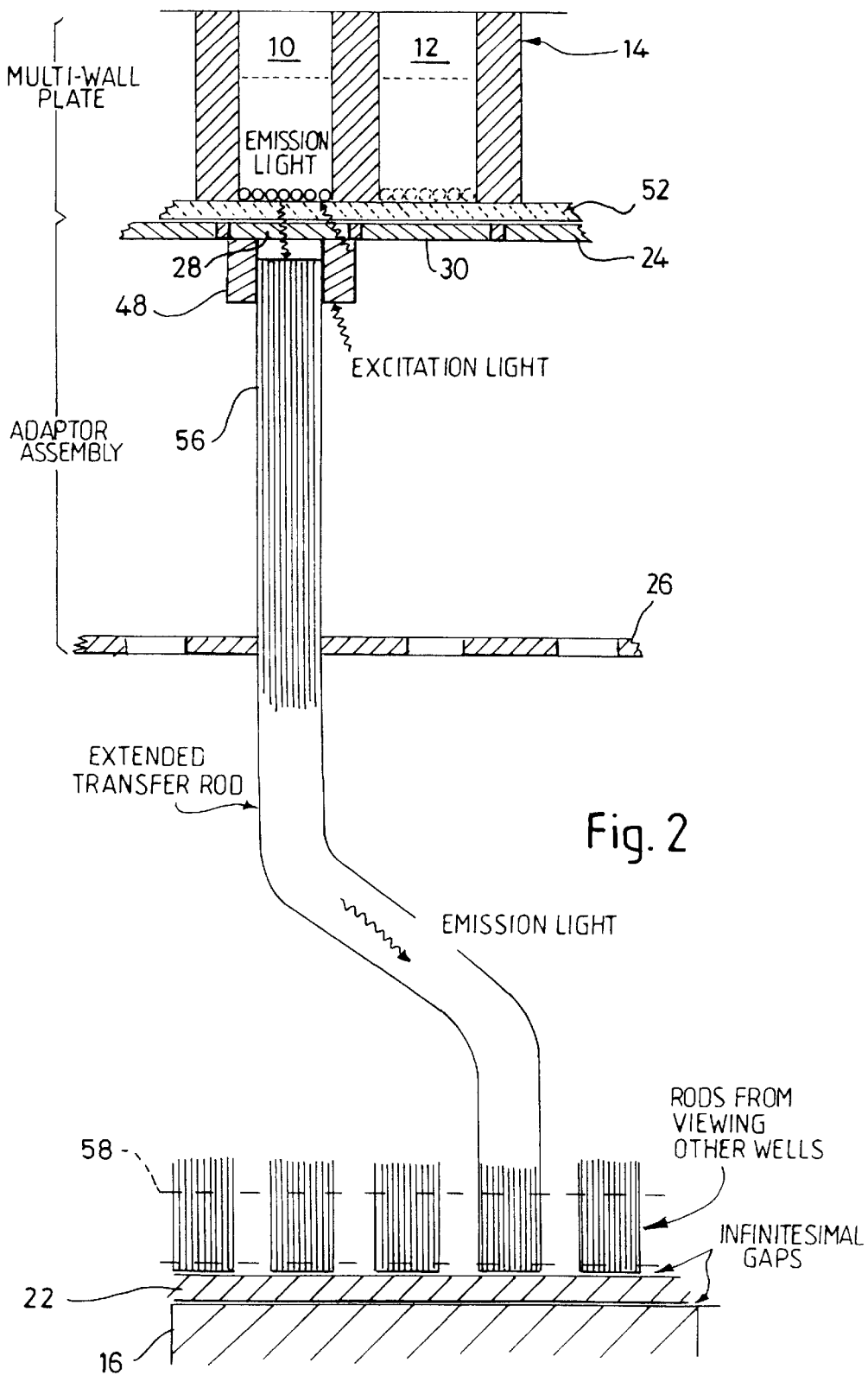
FIG. 2 is a similar schematic view of a modified version of the arrangement shown in FIG. 1.
Figure 2A:
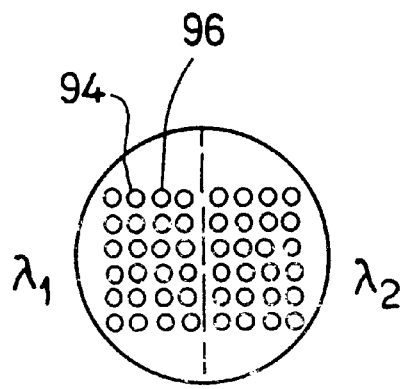
Figure 2B:
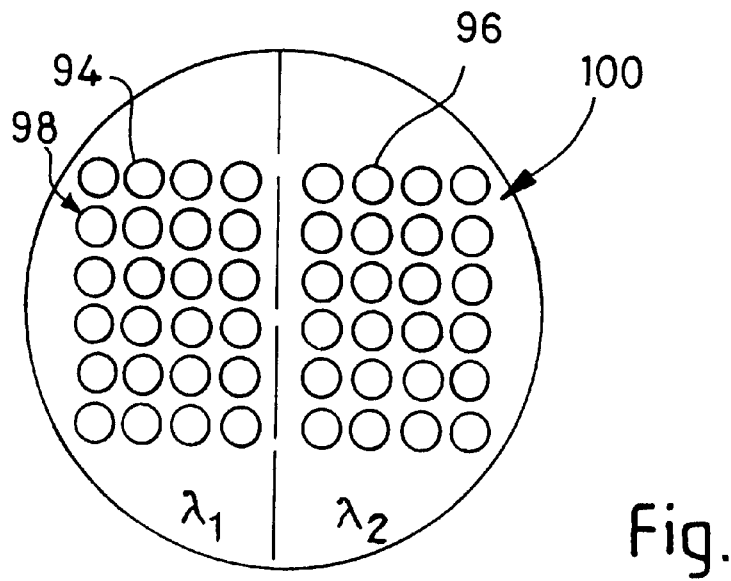

In FIG. 2 the same reference symbols have been used as in FIG. 1 to denote similar items but the fibre optic bundle 20 is now designated by reference numeral 56, since instead of terminating at the lower plate 26, the fibre optic bundle carries on through the plate 26, and is re-arranged in position relative to the other fibre optic bundles extending through the plate 26, so as to be positioned as required adjacent the input face of the filter 22. In order to maintain the registration of the output ends of the fibre optic bundles such as 56, an exit plate 58 (shown in dotted outline), is provided with appropriate apertures within which the lower ends of the fibre optic bundles 56 are embedded.

Where the field of view of the camera has an aspect ratio of say 4:3, the array of fibre optic bundles in the plate 58 is arranged so as to approximate to that ratio. Where there are 96 wells and 96 fibre optic bundles, the latter may be arranged in 12 rows, each containing 8 bundles. In this way the image presented to the camera can be optimised.

If the area available at the camera input is insufficient to accommodate the total area of the fibre optic bundles presented thereto, the optical fibres making up each bundle may be tapered in cross-section from the input to output, so that the area of the bundle presented to the filter is smaller than the area of the fibre optic bundle presented to the well plate. This allows for a greater packing density of fibre optic bundles at the camera input. However it may also result in light loss and other undesirable optical effects and alternative techniques are preferred.

Figure 3:
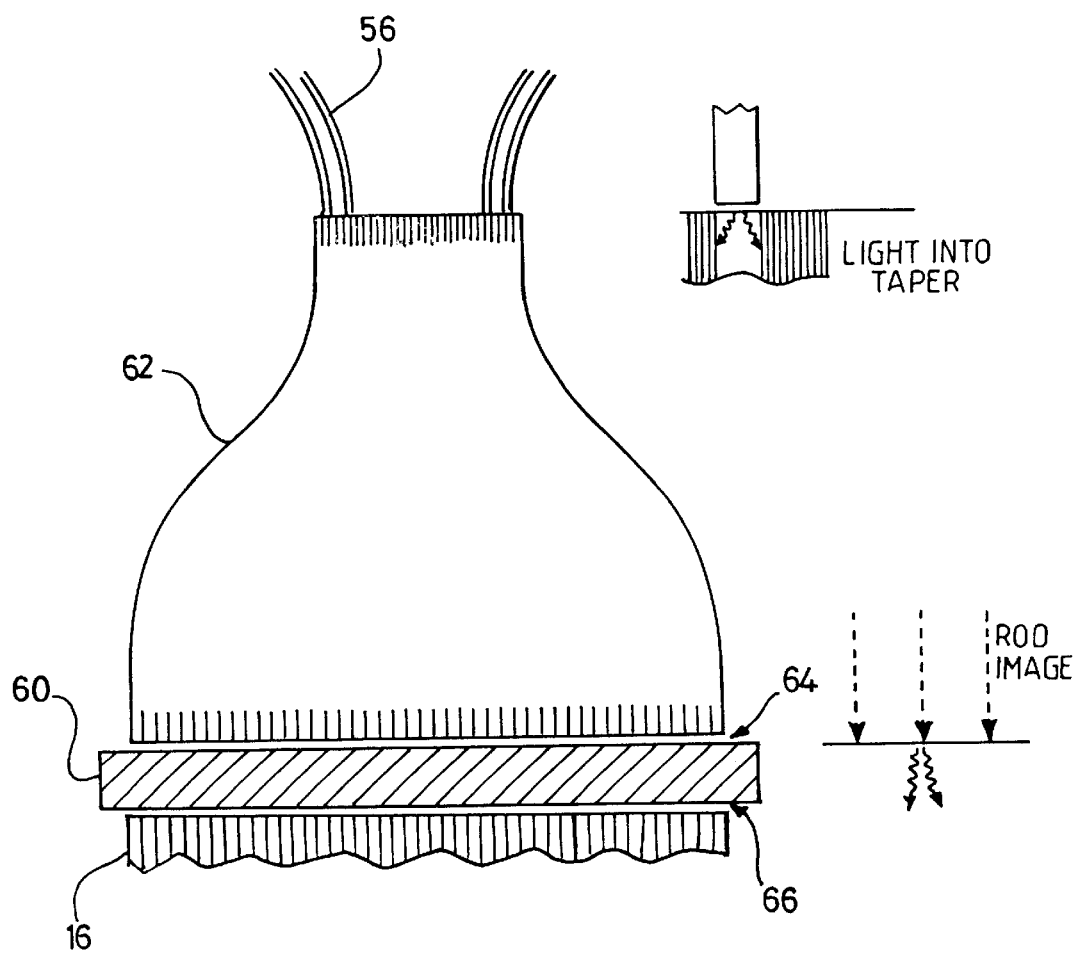
FIG. 3 is a schematic view of a modification in accordance with the present invention, to take advantage of an interference filter.

FIG. 3 illustrates an embodiment in accordance with the present invention, which is to advantage when the filter 22 is an interference filter. Such a filter is shown at 60 in FIG. 3 adjacent the camera input window 16.

Interference filters only function properly with substantially parallel input rays. In practice it has been found that an angular spread of up to 12 degrees can be permitted but the angular spread of light leaving the output end of a fibre optic such as 56 in FIG. 2 will tend to be more like 36°.

The arrangement of FIG. 3 reduces the angular spread by progressively enlarging each fibre optic cross-section so that its diameter is increased by a factor of 3.

Theoretically each of the optical fibres making up the fibre optic bundles such as 56 may be increased in diameter, individually. However more practically, a separate so called fibre optic "taper" may be used such as shown in FIG. 3 and denoted by reference numeral 62. This comprises a large number of individual fibres each of which increases in diameter from input to output, so as to provide the 3:1 ratio indicated above. The fibre optic bundles such as 56 are terminated at the input surface of the taper 62 so that any light emanating therefrom is captured by the input ends of the fibres making up the taper, and is transferred to the appropriate output face of the taper.

Where relative positions of the fibres in the input and output faces of the taper is substantially constant, the light image presented by the output face of the taper 62 is an enlarged version of the light pattern presented thereto by the fibre optic bundles 56.

On the other hand the angular spread of rays leaving any fibre optic end in the output faceplate of the taper 62 is approximately one third that of the acceptance angle at the opposite input face of the taper, so that whereas at the input face the angular spread of rays can be of the order of 36°, at the output face the angular spread is of the order of 12°or less.

Small air gaps at 64 and 66 permit the filter 60 to be moved laterally from between the camera and taper and for another similar filter to be positioned therebetween.

Figure 3A:
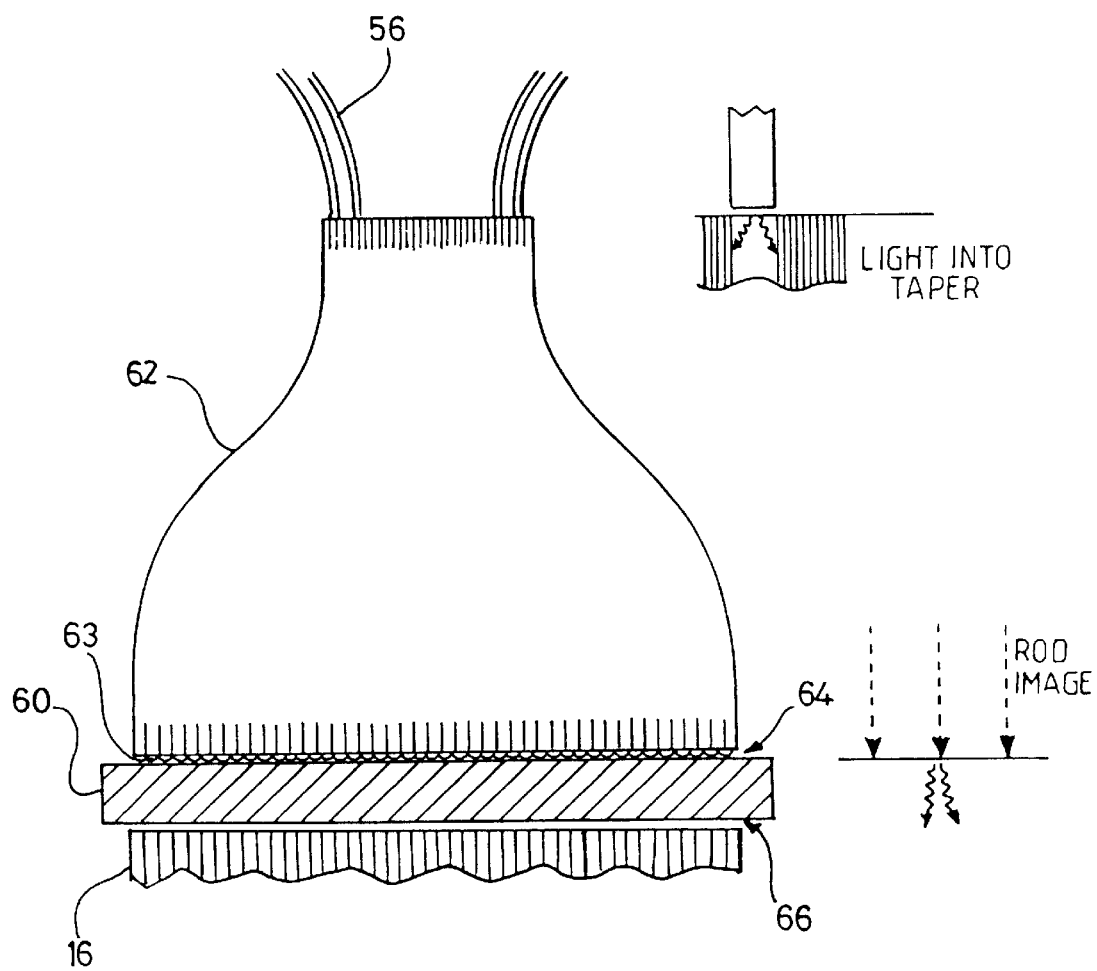
FIG. 3A is a modified version of the schematic view of FIG. 3, with the lens shown on the underside of the taper.

An alternative arrangement shown in FIG. 3A employs a mini lens or, preferably a GRIN lens 63, at the end of each of the optical fibre bundles such as 56, in FIG. 2, which makes up the taper 62, so that an enlarged image of the end of each optical fibre is. "seen" by the filter 22. Unfortunately a lens approach is wavelength dependent. Vignetting can occur; there is a limited numerical aperture acceptance, and it is difficult to restrict the angular range of skew rays or rays coming from the edges of the fibre optic bundles. There is also the need for careful alignment of the lenses with the fibre optic bundles.

The arrangement shown in FIG. 3 is therefore the more preferred solution since it is free of almost all of the problems mentioned above.

Figure 4:
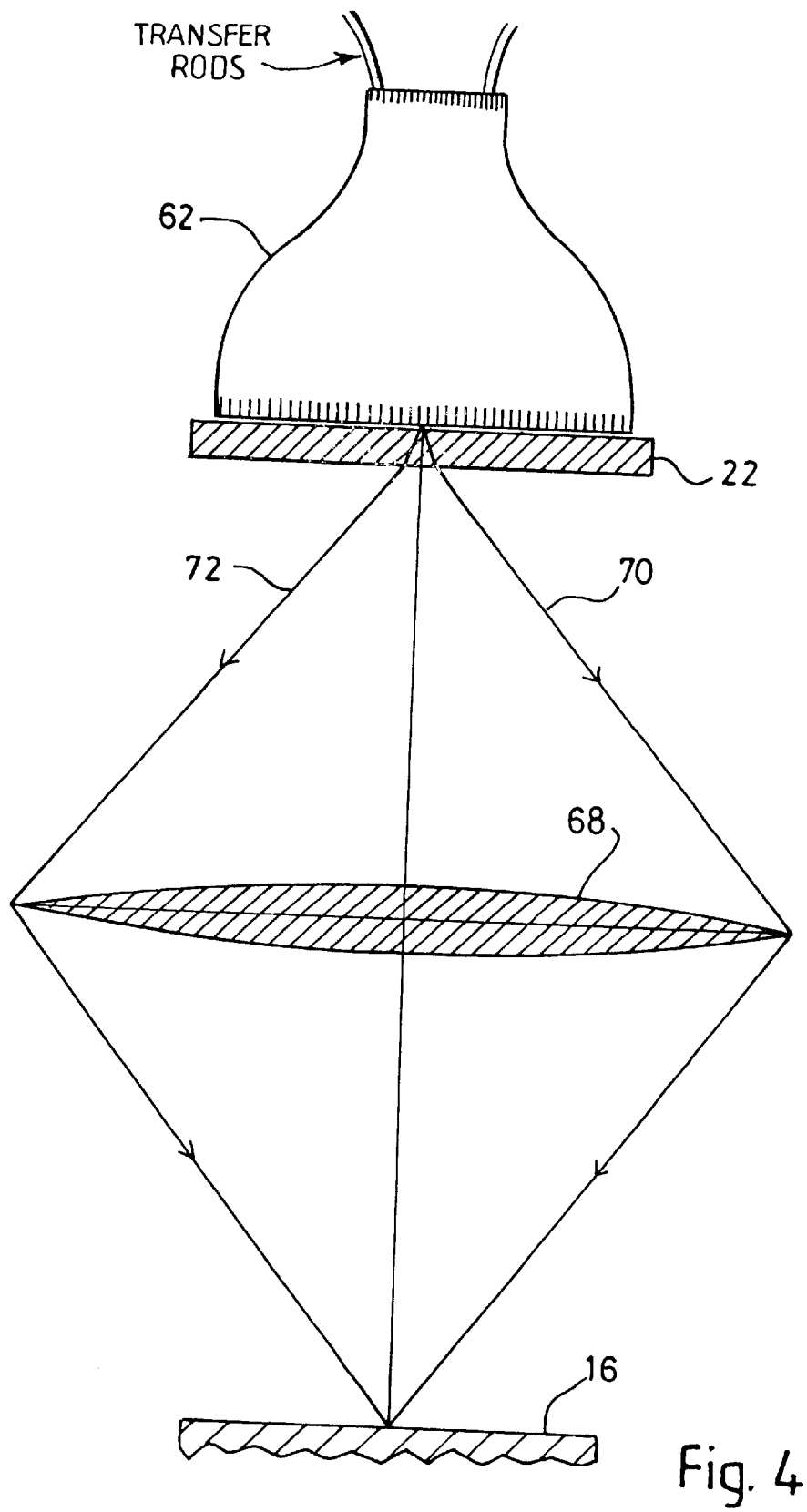
FIG. 4 is a schematic view showing how a lens can be positioned between the interference filter and the camera input to remove extreme stray and skew rays from the camera input.

Unfortunately stray skew rays are not necessarily eliminated using a taper such as 62, and FIG. 4 illustrates a further modification in which the limited light gathering efficiency of a lens is used to advantage, so as largely to eliminate unwanted stray and skew rays thereby reducing cross-talk between fibre optic bundles, and light with large wavelength shifts.

In FIG. 4 a lens 68, having an appropriate numerical aperture, is positioned between the interference filter 22 and the camera input 16. Typically the lens, filter and camera are positioned so as to achieve approximately unity magnification and from the ray paths shown at 70 and 72 it will be seen that whereas the lens accepts most of the light leaving the interference filter within 12° measured in air, it will not "see" light having a greater angular spread, so that unwanted extreme stray and skew rays will fail to be focused onto the camera input 16.

The effect of the lens 68 is therefore to clean up the image presented to the camera and whilst there will be a little loss of light, the advantage greatly outweighs the disadvantage.

A further advantage arises from the fact that the air gap between the lens and the filter is considerable and a larger gap between the output of the taper 62 and the input to the filter 22 also may be permitted.

Figure 5:
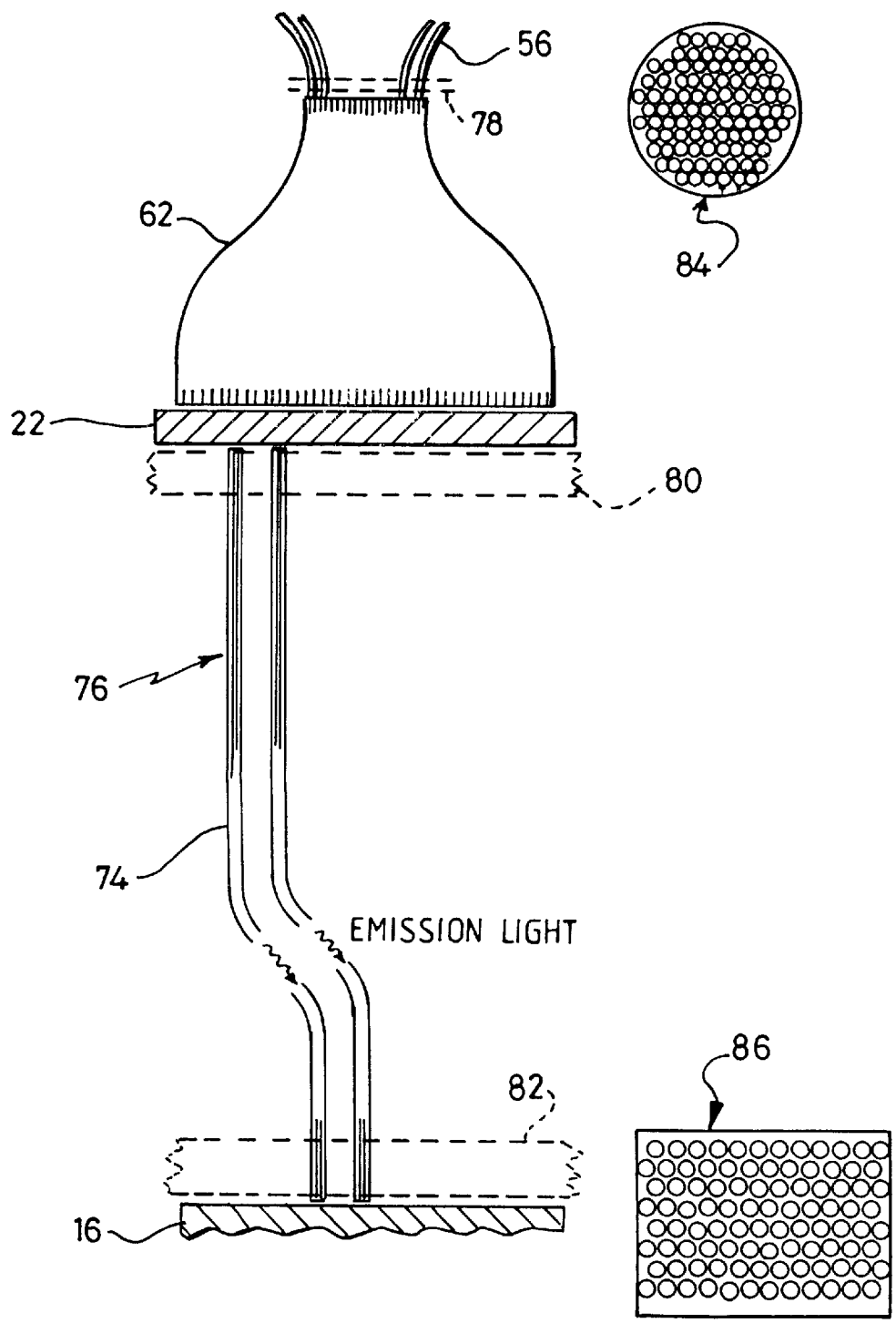
FIG. 5 illustrates a further arrangement in which the lens is replaced by fibre optic coupling, for the same purpose, and further enables optimisation of the optical system to be achieved.

FIG. 5. illustrates a further refinement in which the lens 68 is replaced by a fibre optic transfer device.

In the simplest case, a fibre optic plate is simply positioned between the output of the interference filter and the input of the camera. No magnification or demagnification occurs, but because the fibre optic plate will transmit less and less on the angle of the rays increases, so an effect similar to that obtained by using the lens 68, can be achieved, in that the image presented at the output of the fibre optic plate will be a "cleaned up" version of that presented to the plate from the filter 22.

However the FIG. 5 arrangement allows a further advantage to be gained in that it is now possible to ignore the restraints imposed by the aspect ratio of the field of the view of the camera, on the arrangement of the fibre optic bundles presenting the image to and recovering the light from the interference filter, and to this end the fibre optic bundles such as 56 are arranged optimally over the entire area of the output of the taper 62, so as to occupy the whole area of the filter 22. The fibre optic bundles, (one of which is denoted by reference numeral 74 in FIG. 5), which collect the light from the output of the filter and convey it to the camera input are arranged so as to collect the light optimally from over the output face of the filter but are re-arranged so as to present it optimally in the correct aspect ratio to the input of the camera 16.

If desired, the fibres making up the bundle such as 74 may taper from one end to the other so as to produce a magnified or demagnified image of the light pattern presented thereto from the filter 22.

It is not essential to consider using fibre optic bundles such as 74 in the coupling 76 between the filter and the camera. Instead a simple fibre optic plate may be used (which may or may not comprise a taper), since its purpose is merely to present the light image outputted by the filter, to the camera. Also shown in FIG. 5 are the support plate arrangements shown in dotted outline at 78, 80 and 82 respectively for maintaining in correct alignment and spacing the fibre optic bundles 56 in the case of plate 78, and the optical fibre or fibre optic bundles such as 74 adjacent the interference filter (in the case of plate 80) and adjacent the camera input (in the case of plate 82).

The optimised arrangement of fibre optic bundles (56) for presentation to the input face of the taper 62 is shown at 84. This essentially comprises a plan view of the plate 78. The corresponding re-arrangement of optical fibre bundles (74) to form an approximation to a 4:3 aspect ratio, is illustrated at 86. This is essentially a plan view of the plate 82 as seen by the camera 16.

The output of the taper 62 presents an enlarged image of 84 to the filter 22 and for optimal efficiency the input ends of the fibre optic bundles 74, and held in place by the plate 80, are arranged so to correspond precisely to the regions in the output face of the taper 62 which are illuminated by light from the fibre optic bundles such as 56. In this way although there is a degree of redundancy in terms of optical fibres within the taper 62, fibre optic paths through bundles such as 74 provide the only light path between plate 80, and plate 82, and therefore the camera input at 16. This tends to further improve the elimination of extreme, skew and stray rays from the light presented to the camera.

Whilst in theory the arrangement of the fibre optic bundles and therefore the apertures through the plate 80 can be mapped by simply enlarging the plate 78 by an appropriate factor, this does presuppose that the fibres making up the taper 62 accurately map the input to the output face. Since there may be a degree of rotation or skew as between one face and the other of the taper, a more accurate mapping of the positions to be occupied by the upper ends of the fibre optic bundles (74) can be obtained by placing unexposed photographic film over the output of the taper and uniformly illuminating all of the fibre optic bundles (56), so as to expose a pattern of light spots to the photographic film. After exposure the film can be developed to produce a one to one photographic image of where the fibre optic bundles 56 are projected by the taper 62. The developed film can be used as a template to form the apertures in the plate 80, into which the upper ends of the fibre optic bundles (74) can be secured.

Since it will be important, the registration of the film to the output face of the taper 62 must be noted so that when the exposed and developed film is presented as a template, the correct registration of the plate 80 can also be ascertained. Provision must be made to make sure that the plate 80 is presented in exactly the appropriate registration and alignment with the end face of the taper so as to maintain the optical alignment of the fibre bundles such as 74.

The only difference in practice will be the presence of the filter 22 which simply causes the plate 80 to be spaced from the output face of the taper 62 by the appropriate amount to permit the filter to be positioned therebetween.

Figure 6:
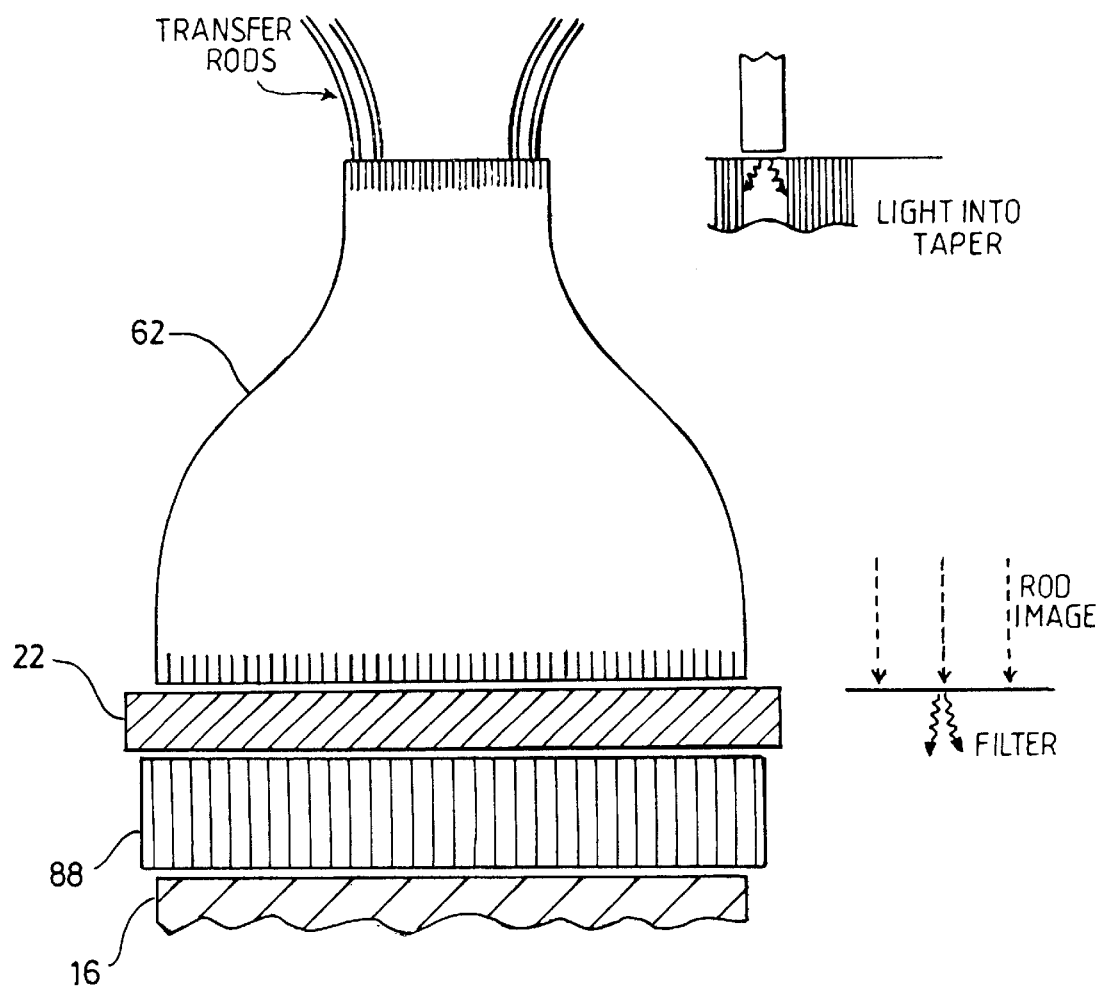
FIG. 6 illustrates one example of a low NA transfer plate for inhibiting skew rays.

In FIG. 6 an angle collimating plate 88 is shown located between, the interference filter 22 and the camera input face plate 26. The plate 88 is preferably a fused bundle of optical fibres each having a numerical aperture of the order of 0.2.

Figure 7:
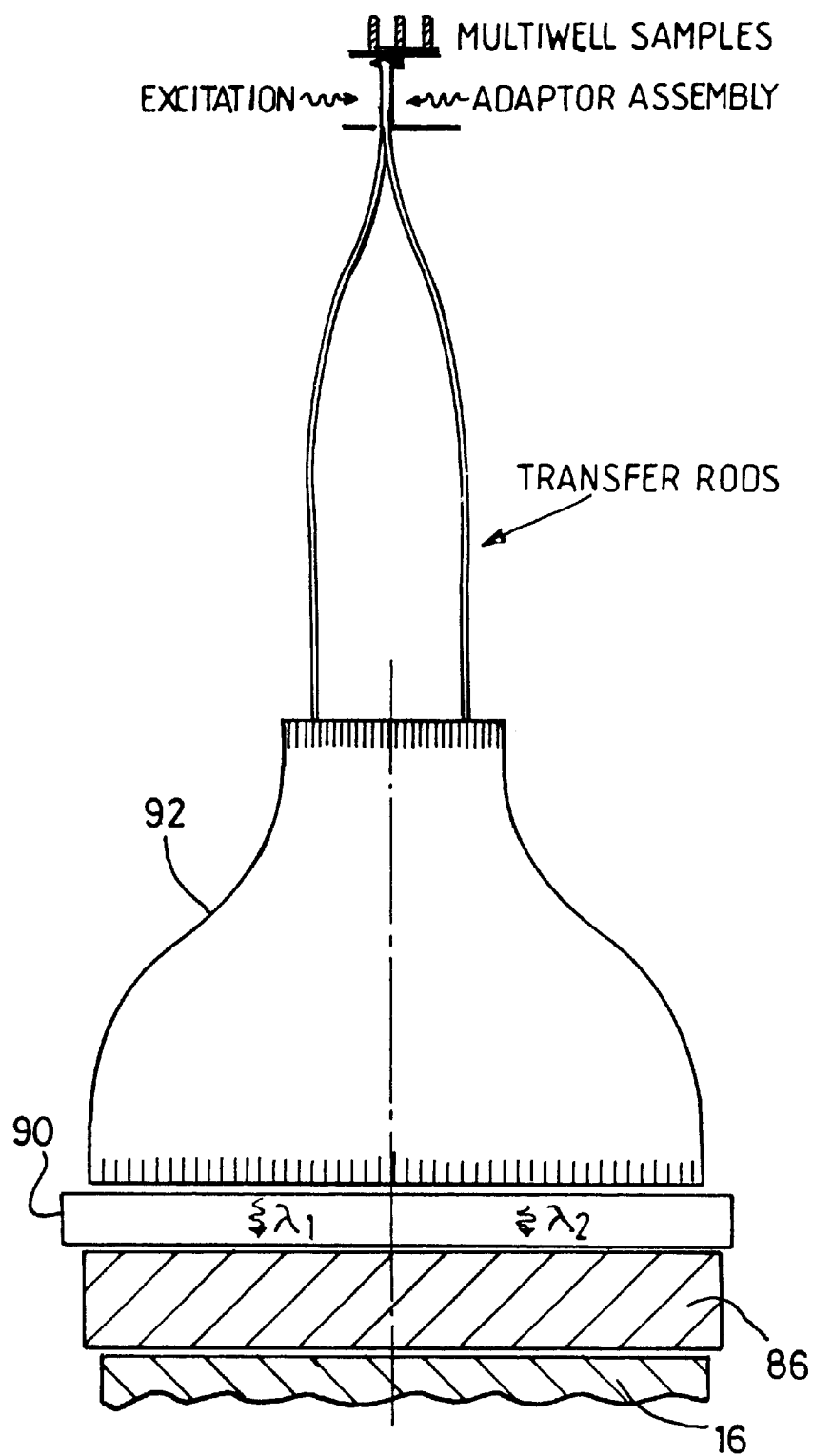
FIGS. 7 and 8 illustrate two different arrangements for achieving simultaneous evaluation of two different wavelength emissions from a sample.

FIG. 7 is similar to FIG. 1 in that it also includes plate 86, but here the interference filter 90 is divided into two regions one selective around λ1 and the other selective around λ2.

The fibre optic taper 92 may be the same as item 62 of FIGS. 4 and 5 hitherto described, or more preferably is such that adjoining fibres such as 94, 96 making up the input face thereto (see FIG. 7A) are directed one into the region 98, and the other into the region 100, of the output face thereof (see FIG. 7B).

Figure 8:
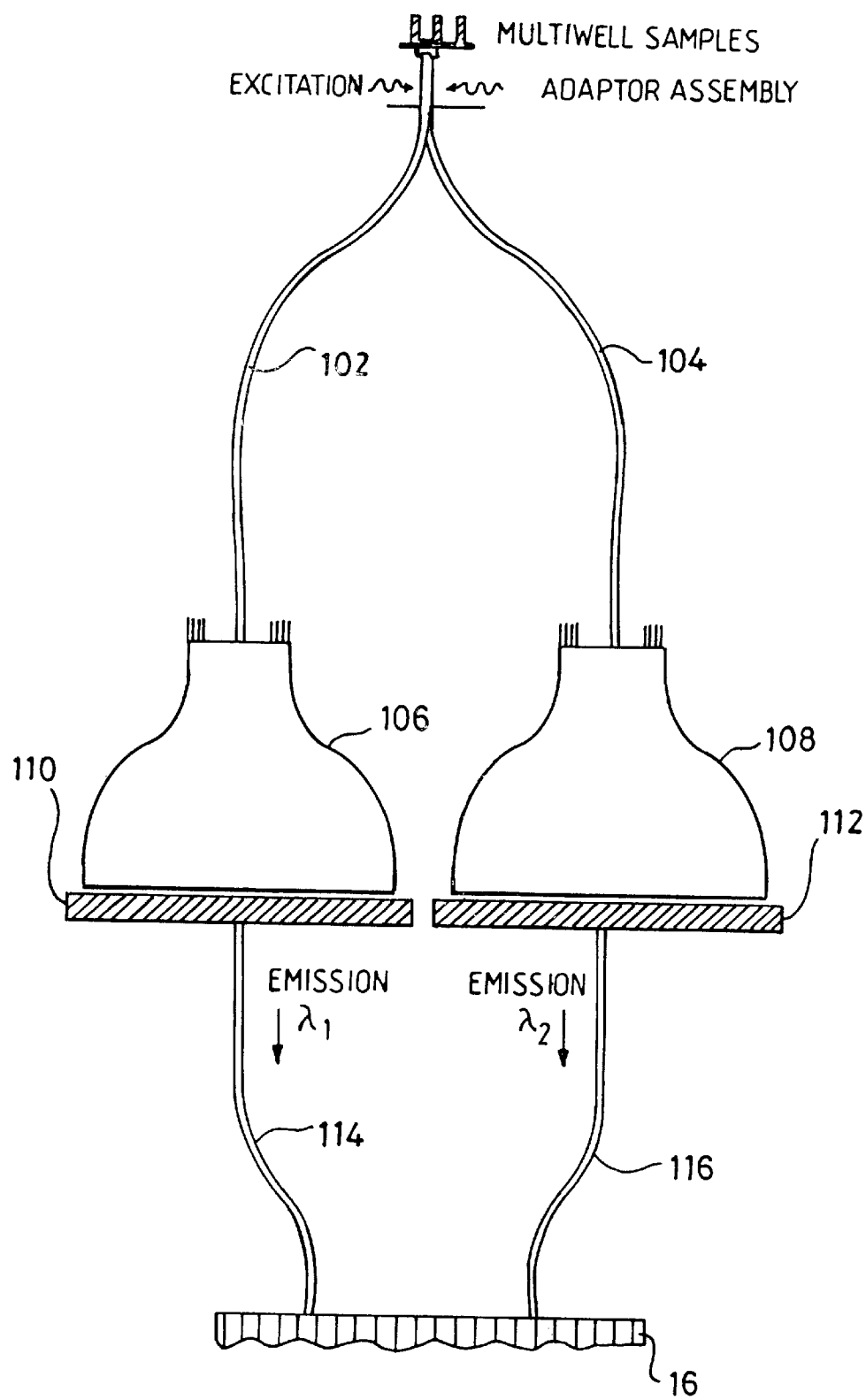

FIG. 8 extends the idea embodied in FIG. 7, and illustrates how half of the fibres (or fibre bundles) 102 making up the transfer rods 56 of FIG. 5 can be directed to one, and the other half 104 to the other, of two fibre optic tapers 106, 108 respectively. The light output of taper 106 is filtered by filter 110 and that of 108 by filter 112 and transfer rods (fibres of bundles as appropriate), of which examples only are shown at 114, 116, convey the filtered light to the input faceplate of a CCD camera 16.

Where the camera aspect ratio is fixed and the area and/or aspect ratio of the filters is inappropriate for that of the camera, the rods 114, 116 etc, may be rearranged as between input and output of the rod array, so as to alter the aspect ratio as between input and output, to better accommodate that of the camera.

A plurality of pairs of filters such as 110, 112 may be mounted in a filter wheel (not shown) rotatable relative to the tapers (106, 108), and the rod array (114, 116), to present different pairs of filters as required.

What is claimed is:
1. An imaging system for conveying light produced by fluorescence within each of a plurality of sites in a multi-site sample, to a photodetector, wherein fluorescence occurring at one wavelength is distinguished from that occurring at another wavelength by the use of an interference filter, and in which:
 1) the photodetector is a two dimensional CCD array camera with an input faceplate;
 2) a plurality of optical fibre bundles each having a cross sectional area commensurate with that of each site are located with the bundle ends adjacent the said sites, each bundle communicating with one of the sites;
 3) a plate is provided, adapted to register the ends of the bundles relative to one another and to the sites; and
 4) an angle collimating device is positioned between the other ends of the bundles and the camera faceplate to reduce the transmission of skew rays to the camera.

2. An imaging system as claimed in claim 1, in which the angle collimating device comprises a fibre optic device in which each of the optical fibre forming the device has a numerical aperture the value of which is sufficiently low as to reduce the transmission of skew rays incident thereon.

3. An imaging system as claimed in claim 2, in which the angle collimating device is incorporated into the fibre optic camera faceplate.

4. An imaging system as claimed in claim 1, in which each fibre optic bundle is divided into two sub-bundles and the sub-bundles are grouped to form two light paths so that fluorescence from the sites is conveyed along the two different paths to two different interference filters and bundles of optical fibre convey light transmitted by the filters to two different regions of the camera faceplate.

5. An imaging system as claimed in claim 1, in which a fibre optic taper is located between the output ends of the bundles and the filter, in which the larger end of the taper faces the filter.

6. An imaging system as claimed in claim 1, wherein air gaps exist between the filter and each adjoining optical element to permit the filter to be removed and replaced by another.

7. An imaging system as claimed in claim 5, including a converging lens located between the filter and the camera faceplate.

8. An imaging system as claimed in claim 5, including an array of fibre optic bundles located between the filter and the camera faceplate, with air gaps between the opposed faces of the optical elements.

9. An imaging system as claimed in claim 1, in which an interference filter is located between the said other ends of the bundles and the camera faceplate.

10. An imaging system for conveying light produced by fluorescence within each of plurality of sites in a multi-site sample, to the input of a photodetector, wherein fluorescence occurring at one wavelength is distinguished from that occurring at another wavelength by the use of interference filter, and in which:

1) the photodetector is a two dimensional CCD array camera;
2) a plurality of optical fibre bundles each having a cross-sectional area commensurate with that of each site are located with the input ends adjacent the said sites, each bundle communicating with one of the sites; and
3) each of the fibre bundles is divided into two sub-bundles of fibre which convey light from each of the sites to each of two different wavelength interference filters or two different wavelength selective regions of a single interference filter, to select between different wavelengths.

11. An imaging system for a fluorescence array comprising fibre optic coupling means for transmitting fluorescence emissions from sites in a plural site sample towards a photodetector in combination with interference filter means for selecting fluorescence for transmission to the photodetector according to wavelength, and in which:

1) the photodetector is a two dimensional CCD array camera onto which light from a plurality of different sites can be directed simultaneously to occupy different parts of the array: and
2) the fibre optic coupling means provides N different paths from each of the sites to N different interference filters, each selecting a different one of N different wavelengths, for onward transmission to the CCD camera.

12. An imaging system for conveying light produced by fluorescence within each of a plurality of sites in a multi-site sample to a photodetector, wherein fluorescence occurring at one wavelength is distinguished from that occurring at another wavelength by the use of an interference filter, and in which:

1) the photodetector is a two dimensional CCD array camera;
2) a plurality of optical fibre bundles each having a cross-sectional area commensurate with that of each site are located with the bundle ends adjacent the said plurality of sites, each bundle communicating with one of the sites; and
3) the output ends of the fibre bundles are located adjacent an interference filter and are arranged differently from the arrangement of the input ends of the bundles adjacent the sample site.

13. An imaging system as claimed in claim 12, including optical means which reduce the numerical aperture at the output of the fibre bundles as seen by the interference filter.

14. An imaging system as claimed in claim 13, in which the optical means comprises a mini-lens or gradient index lens at the end of each fibre bundle.

15. An imaging system as claimed in claim 13, in which the optical means comprises an optical fibre taper.

16. An imaging system as claimed in claim 13, wherein an angle collimating plate is located in the light path between the sample and the camera faceplate to reduce the transmission of skew rays to the camera.

* * * * *